(12) United States Patent
Watanabe et al.

(10) Patent No.: US 7,407,325 B2
(45) Date of Patent: Aug. 5, 2008

(54) METHOD AND APPARATUS FOR MEASURING THERMOPHYSICAL PROPERTIES

(75) Inventors: Hiromichi Watanabe, Ibaraki (JP); Tetsuya Baba, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 82 days.

(21) Appl. No.: 11/214,052

(22) Filed: Aug. 30, 2005

(65) Prior Publication Data
US 2006/0039443 A1    Feb. 23, 2006

(51) Int. Cl.
*G01J 5/00* (2006.01)
*G01N 25/20* (2006.01)

(52) U.S. Cl. .............................. 374/43; 374/9; 374/121
(58) Field of Classification Search .................. 374/43, 374/9, 121
See application file for complete search history.

(56) References Cited

U.S. PATENT DOCUMENTS

| | | | | |
|---|---|---|---|---|
| 5,713,665 | A * | 2/1998 | Kato et al. | 374/43 |
| 7,038,209 | B2 * | 5/2006 | Opfermann et al. | 250/341.6 |
| 2002/0080850 | A1 * | 6/2002 | Baba | 374/43 |
| 2005/0002435 | A1 * | 1/2005 | Hashimoto et al. | 374/43 |
| 2006/0153269 | A1 * | 7/2006 | Lakestani et al. | 374/43 |

FOREIGN PATENT DOCUMENTS

| | | |
|---|---|---|
| JP | 03-238345 | 10/1991 |
| JP | 10-123075 | 5/1998 |
| JP | 2001-083113 | 3/2001 |
| JP | 20020-122559 | 4/2002 |
| JP | 2003-065982 | 3/2003 |
| JP | 2004303466 A * | 10/2004 |

OTHER PUBLICATIONS

Parker, et al., "Flash Method of Determining Thermal Diffusivity, Heat Capacity, and Thermal Conductivity", Sep. 1961, Journal of Applied Physics, vol. 32, No. 9, pp. 1679-1684.*
Baba et al., "Improvement of the laser flash method to reduce uncertainty in thermal diffusivity measurements", Nov. 6, 2001, Meas. Sci. Technol., vol. 12, pp. 2046-2057.*
Cezairliyan, Ared, *Design and Operational Characteristics of a High-Speed (Millisecond) System for the Measurement of Thermophysical Properties at High Temperatures*, Journal of Research of the National Bureau of Standards—C. Engineering and Instrumentation, vol. 75C, No. 1, Jan.-Mar. 1971, pp. 7-18.
Righini, F. et al., *Thermal Conducivity by a Pulse-Heating Method: Theory and Experimental Apparatus*, International Journal of Thermophysics, vol. 11, No. 4, 1990, pp. 629-641.

* cited by examiner

*Primary Examiner*—Gail Verbitsky
*Assistant Examiner*—Mirellys Jagan
(74) *Attorney, Agent, or Firm*—Morgan, Lewis & Bockius LLP

(57) ABSTRACT

The present invention provides a method for measuring thermophysical properties that includes: rapid resistive self-heating of a specimen by using a heating current; emitting a light to the specimen heated by the rapid resistive self-heating of the specimen; measuring a temperature change of the specimen induced by emitting the light to the specimen; and deriving a thermal diffusivity of the specimen from the temperature change induced by emitting the light to the specimen.

6 Claims, 5 Drawing Sheets

MEASUREMENT OF THERMAL DIFFUSIVITY
BY FLASH METHOD

US 7,407,325 B2

METHOD AND APPARATUS FOR MEASURING THERMOPHYSICAL PROPERTIES

FIELD OF THE INVENTION

The present invention relates to a method and an apparatus for measuring some kinds of thermophysical properties at once, which include the specific heat capacity, the hemispherical total emissivity, the thermal conductivity and the thermal diffusivity, of a material at high temperatures.

BACKGROUND OF THE INVENTION

In order to perform a heat transfer analysis for an apparatus that generates heat or for an apparatus used at a high temperature, four thermophysical properties (e.g., specific heat capacity, hemispherical total emissivity, thermal conductivity and thermal diffusivity) of the materials of which the apparatus is made are required. In case that the apparatus is composed of newly developed materials, or those for which reliable data of thermophysical properties are not available, the above described thermophysical properties of the materials need to be experimentally obtained. Since these four thermophysical properties are generally measured using separate apparatuses, multiple expenditures of time and money are required to obtain all the thermophysical properties. Further, if a specimen is heated to temperatures beyond 1000° C. many times to measure all the thermophysical properties, either the physical properties of the specimen will change or deterioration of the measurement apparatus will occur.

In the 1970s, Cezairliyan et al. in the United States developed a method whereby the specific heat capacity and the hemispherical total emissivity of a conductive material at a temperature beyond 1000° C. were measured rapidly using a single measurement apparatus (see Reference 1). The feature of this measuring method is the way to heat a specimen. According to this method, when electric charges stored in a battery or in a capacitor having a large capacity were applied to a conductive specimen, the temperature of the specimen could be raised to 3000° C. or higher in 0.2 seconds by Joule heat which is induced by a large pulsed current that flows through the specimen.

In this measuring method, the temperature of the sample and the Joule heat generated in the specimen are measured during the rapid resistive self-heating and during the subsequent cooling of the specimen. Then, the specific heat capacity and the hemispherical total emissivity are calculated using a heat balance relationship between the Joule heat, the heat capacitance and the heat radiated by the specimen. This measuring method is employed only for electrically conductive materials; nevertheless, this was an remarkable method that can be used to rapidly measure thermophysical properties at temperatures beyond 2000° C., which it previously had been very difficult to measure, and that can minimize measurement errors due to changes in the qualities of a specimen and deterioration of the measurement apparatus and can considerably reduce measurement costs.

However, with this measuring method, the thermal conductivity and thermal diffusivities required for a heat transfer analysis can not be measured, and these property values must be measured separately. To resolve this problem, Righini et al. in Italy has developed a method whereby, for a specimen, a change in the temperature distribution with reference to time during rapid resistive self-heating and the subsequent cooling of the specimen is measured to determine the thermal conductivity together. However, since the thermal conductivity is calculated based on an assumption that is not always self-evident, this method has not yet been commonly employed.

In principle, a thermal conductivity is defined as the product of the specific heat capacity, the density and the thermal diffusivity.

In most cases, since the temperature dependency of the density of a solid is very small compared with the temperature dependency of the thermal conductivity or the specific heat capacity, the thermal conductivity at a high temperature is generally calculated based on the density at room temperature and the thermal diffusivity, and the specific heat capacity each measured at the temperature. At present, the thermal diffusivity of a solid is generally measured by using a flash method.

[Reference 1] A. Cezairliyan, J. L. McClure, C. W. Beckett: J. Res. National Bureau of Standards, Vol. 75C-1 (1971), pp. 7-18.

However, the upper limit temperature where the flash method is available is approximately 2700° C., because the temperature of the specimen is generally controlled by using a resistance furnace. Further, changes in the qualities of a specimen or deterioration of a measurement apparatus, as described above, will adversely affect the measurement.

In view of the above, an object of the present invention is to provide a method to measure the specific heat capacity, the hemispherical total emissivity, the thermal conductivity and the thermal diffusivity at once during a rapid resistive self-heating of the specimen, and whereby these physical properties can be measured even at a high temperature at which measurements can not be conducted by a conventional method, and an apparatus for employing this measuring method.

SUMMARY OF THE INVENTION

To solve the above-indicated objection, in the present invention, light is emitted to a specimen held at a predetermined constant temperature by a rapid resistive self-heating of the specimen, and a temperature change of the specimen caused by the emission of light to the specimen is measured by a radiation thermometer, then a thermal diffusivity of the specimen is derived therefrom. Furthermore, a temperature of the specimen held at a constant temperature before emitting the light to the specimen, an electric power consumed for the specimen and a temperature change with reference to time during the rapid resistive self-heating period before the temperature is maintained at the constant temperature are measured, and the specific heat capacity and the hemispherical total emissivity of the specimen are derived therefrom (see Reference 2). Based on the principle relationship described above, the thermal conductivity is calculated from the measured thermal diffusivity, specific heat capacity and density. As a result, all data of the thermophysical properties required for a thermal transfer analysis are obtained.

In addition, in order to obtain more accurate data of a thermal conductivity, it is preferable that the size of a specimen is measured to determine the density while the temperature of specimen is maintained at a constant.

Namely, the present invention is mainly directed to the following items:

(1) A method for measuring thermophysical properties that comprises: rapid resistive self-heating of a specimen by using a heating current; emitting a light to the specimen heated by the rapid resistive self-heating; measuring a temperature change of the specimen induced by emitting the light to the specimen; and deriving a thermal diffusivity of the specimen from the temperature change induced by emitting the light to the specimen.

(2) The method for measuring thermophysical properties according to item (1), wherein the heating current is a pulse current that is generated by discharging a capacitor or a battery each connected in series with the specimen.

(3) The method for measuring thermophysical properties according to item (1), wherein the heating current is controlled by a field-effect transistor.

(4) The method for measuring thermophysical properties according to item (1), wherein the light is a single pulse of light.

(5) The method for measuring thermophysical properties according to item (1), wherein the light is a periodic light.

(6) The method for measuring thermophysical properties according to item (1), wherein the temperature change induced by emitting the light to the specimen is measured with a radiation thermometer.

(7) The method for measuring thermophysical properties according to item (1), wherein the temperature change induced by emitting the light to the specimen is measured by the thermo-reflectance method.

(8) The method for measuring thermophysical properties according to item (1), which further comprises: measuring: a temperature of the specimen when the temperature of the specimen is held at a constant temperature before emitting the light to the specimen; an electric power that is supplied to the specimen when the temperature of the specimen is held at the constant temperature; and a temperature change of the specimen induced by the rapid resistive self-heating of the specimen; deriving a hemispherical total emissivity of the specimen from the experimental data of the temperature and electric power; deriving a specific heat capacity of the specimen from the hemispherical total emissivity and the temperature change induced by the rapid resistive self-heating of the specimen.

(9) The method for measuring thermophysical properties according to item (8), which further comprising: deriving a thermal conductivity of the specimen from the thermal diffusivity, the specific heat capacity and a density of the specimen.

(10) The method for measuring thermophysical properties according to item (8), wherein the temperature of the specimen is controlled under a feedback control so as to have the constant temperature until just before emitting the light to the specimen.

(11) The method for measuring thermophysical properties according to item (10), wherein the heating current is maintained at a value just before the feedback control is halted during the period from the halt of the feedback control to the completion of thermal diffusion within the specimen caused by the emission of the light to the specimen.

(12) The method for measuring thermophysical properties according to item (11), wherein the light is emitted to the specimen while the heating current is maintained at the value just before the feedback control is halted.

(13) An apparatus for measuring thermophysical properties that comprises: a rapid resistive self-heating member for rapid resistive self-heating of a specimen by using a heating current; a light emission member for emitting a light to the specimen heated by the rapid resistive self-heating of the specimen; a temperature measuring member for measuring a temperature change induced by emitting the light to the specimen; and an analysis member for deriving a thermal diffusivity of the specimen from the temperature change induced by emitting the light to the specimen.

(14) The apparatus for measuring thermophysical properties according to item (13), wherein the heating current is a pulse current that is generated by discharging a capacitor or a battery each connected in series with the specimen.

(15) The apparatus for measuring thermophysical properties according to item (13), wherein the heating current is controlled by a field-effect transistor.

(16) The apparatus for measuring thermophysical properties according to item (13), wherein the light is a single pulse of light.

(17) The apparatus for measuring thermophysical properties according to item (13), wherein the light is a periodic light.

(18) The apparatus for measuring thermophysical properties according to item (13), wherein the temperature change induced by emitting the light to the specimen is measured with a radiation thermometer.

(19) The apparatus for measuring thermophysical properties according to item (13), wherein the temperature change induced by emitting the light to the specimen is measured by the thermo-reflectance method.

(20) The apparatus for measuring thermophysical properties according to item (13), wherein the analysis member further derives a hemispherical total emissivity and a specific heat capacity of the specimen, wherein the hemispherical total emissivity is derived from: a temperature of the specimen when the temperature of the specimen is held at a constant temperature before emitting the light to the specimen; and an electric power that is supplied to the specimen when the temperature of the specimen is held at the constant temperature, wherein the specific heat capacity of the specimen is derived from: the hemispherical total emissivity; and a temperature change of the specimen induced by the rapid resistive self-heating of the specimen.

(21) The apparatus for measuring thermophysical properties according to item (20), wherein the analysis member further derives a thermal conductivity of the specimen from the thermal diffusivity, the specific heat capacity and a density of the specimen.

(22) The apparatus for measuring thermophysical properties according to item (20), wherein the temperature of the specimen is controlled under a feedback control so as to have the constant temperature until just before emitting the light to the specimen.

(23) The apparatus for measuring thermophysical properties according to item (22), wherein the heating current is maintained at a value just before the feedback control is halted during the period from the halt of the feedback control to the completion of thermal diffusion within the specimen caused by the emission of the light to the specimen.

(24) The apparatus for measuring thermophysical properties according to item (23), wherein the light is emitted to the specimen while the heating current is maintained at the value just before the feedback control is halted.

[Reference 2] T. Matsumoto and A. Cezairliyan: Int. J. Thermophys., Vol. 18(1997), pp. 1539-1556.

Figure 1:
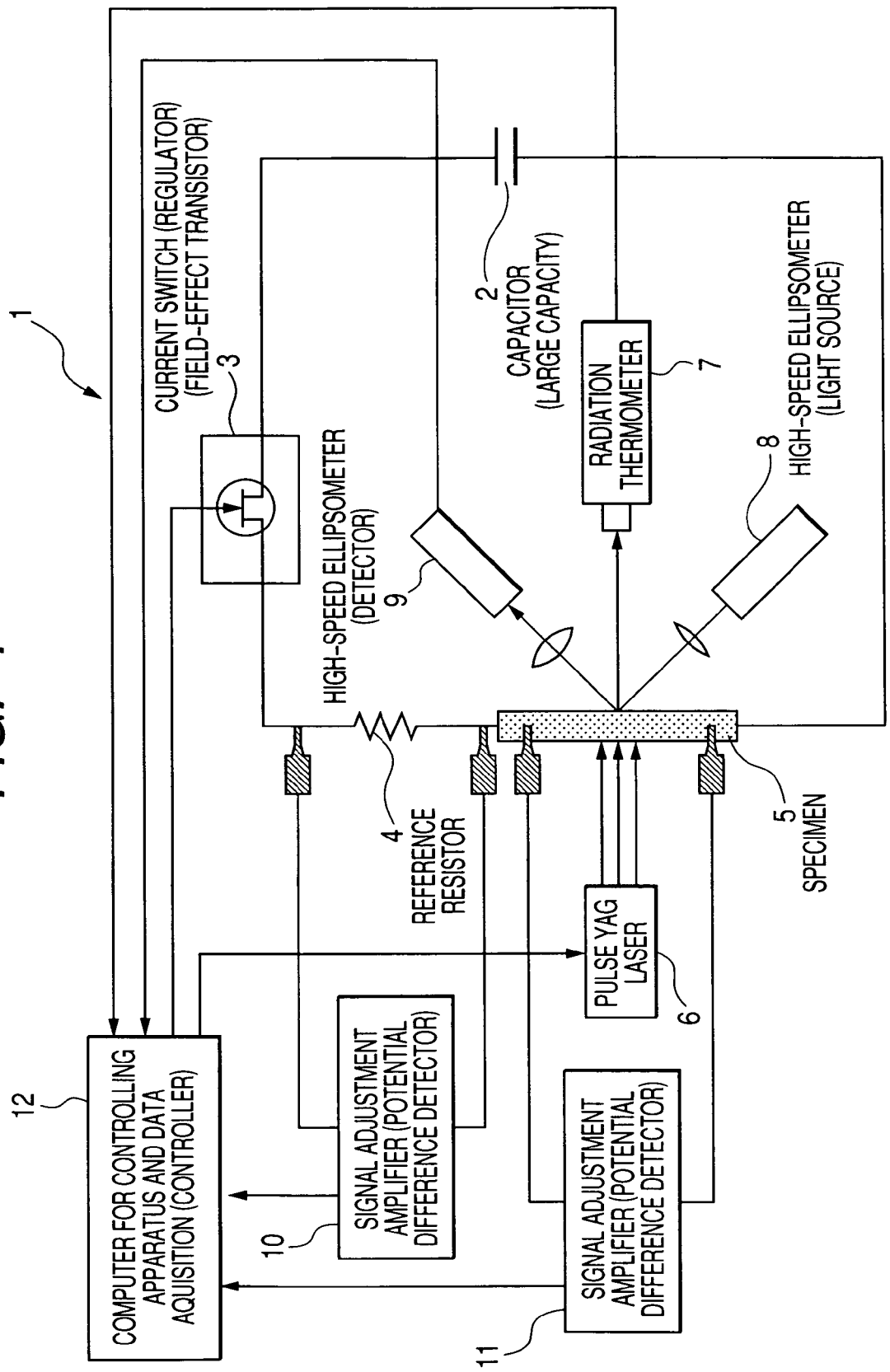
FIG. 1 is a block diagram showing an apparatus according to the present invention and a function thereof.

The reference numerals used in the drawings denote the followings, respectively.

1: high-speed measuring apparatus for thermophysical properties
2: capacitor
3: current switch (regulator)
4: reference resistor
5: specimen
6: pulse YAG laser
7: radiation thermometer
8: light source of high-speed ellipsometer
9: detector of high-speed ellipsometer
10, 11: signal adjustment amplifier
12: computer for controlling apparatus and data acquisition

DETAILED DESCRIPTION OF THE INVENTION

The present invention provides a method for measuring thermophysical properties that comprises: rapid resistive self-heating of a specimen by using a large pulsed current; emitting a light to the specimen being heated by the rapid resistive self-heating of the specimen; measuring a temperature change induced by the emission of the light to the specimen; and deriving a thermal diffusivity of the specimen from the temperature change induced by the emission of light to the specimen so as to measure thermophysical properties such as the specific heat capacity, the hemispherical total emissivity, the thermal conductivity and the thermal diffusivity at once, and whereby these thermophysical properties can be measured even at a high temperature at which measurements can not be conducted by a conventional method.

Furthermore, the present invention provides an apparatus for measuring thermophysical properties that comprises: rapid resistive self-heating member for rapid resistive self-heating of a specimen by using a large pulsed current generated by discharging a capacitor or a battery; a light emission member for emitting a light to the specimen heated by the rapid resistive self-heating of the specimen; a temperature measuring member for measuring a temperature change induced by the emission of the light to the specimen; and an analysis member for deriving a thermal diffusivity of the specimen from the temperature change induced by the emission of the light to the specimen.

In an embodiment of the present invention, the flash method for measuring thermal diffusivity is applied for the method for measuring the specific heat capacity and the hemispherical total emissivity that employs the pulse electrically-heating method, so that a single apparatus can measure the three thermophysical properties at once. Furthermore, thermal conductivity can be also determined from the measured data of thermal diffusivity, specific heat capacity and density.

An embodiment of the present invention is described below. FIG. 1 is a block diagram showing an apparatus for measuring thermophysical properties 1, which employs a rapid resistive self-heating method according to the present invention. A capacitor 2 is a member for accumulating an electric charge used to heat a specimen. When a current switch 3, which is a field-effect transistor, is switched on by a computer for controlling apparatus and data acquisition 12 that serves as a controller, the capacitor 2 supplies a heating current, through a reference resistor 4, to a specimen 5 that is electrically conductive and has a flat plate-shape and thickness of 1 mm or less, so as to employ Joule heating to induce the self-heating of the specimen 5.

In the present invention, the heating current is preferably a pulsed current that is generated by discharging a capacitor or a battery each connected in series with the specimen.

A potential difference between the two terminals of the reference resistor 4 is amplified by a signal adjustment amplifier 10, and the resultant signal is transmitted to the computer for controlling apparatus and data acquisition 12 to measure the magnitude of the heating current flowing through the specimen 5 by the Ohm's law. Further, the potential difference in the specimen 5 is transmitted to the computer for controlling apparatus and data acquisition 12 to measure the magnitude of the voltage applied to the specimen 5. The apparatus preferably has a signal adjustment amplifier 11 to amplify the potential difference in the specimen 5. An insulated-type amplifier is preferably used in view of cutting out a noise. Based on a product of the current and the voltage, the electric power consumed to heat the specimen 5 is calculated, and the electric power is sequentially measured.

The temperature of the thus heated specimen S is measured by a radiation thermometer 7 that employs, as a detection element, a silicon photodiode having time resolutions of several tens of microseconds, and a signal indicating the measured temperature is transmitted to the computer for controlling apparatus and data acquisition 12. A normal spectral emissivity, which is required for converting a radiance temperature measured by the radiation thermometer 7 into a true temperature of the specimen, is sequentially measured by employing a high-speed ellipsometer that does not have a mechanical drive member and then rapidly determines the emissivity.

The computer for controlling apparatus and data acquisition 12 monitors the temperature signal transmitted by the radiation thermometer 7, and controls the quantity of the current flowing through the current switch 3 so as to maintain the specimen 5 at the designated temperature. In the present invention, the current switch 3 that controls the heating current is preferably a field-effect transistor. By employing a field-effect transistor as the current switch 3 and controlling the gate voltage thereof, the specimen heating current, i.e., the specimen temperature is controlled under a high-speed feedback control. In the present invention, the temperature of the specimen is controlled under a feedback control so as to have a constant temperature until just before emitting the light. Further, the heating current is preferably maintained at a value just before the feedback control is halted during the period from the halt of the feedback control to the completion of thermal diffusion within specimen caused by the emission of the light to the specimen, because the temperature of the specimen must not be artificially stabilized during the measurement of thermal diffusivity by a flash method.

During a short period wherein the temperature of the specimen is maintained at a constant temperature, a light is emitted to the specimen 5 to heat the specimen 5. The maintaining of the temperature of the specimen is preferably carried out with an assistance of feedback control as indicated above. In the present invention, the light is preferably a single pulse of light or a periodic light. Further, a temperature change induced by the emission of the light to the specimen is preferably measured by a radiation thermometer, and is measured by the thermo-reflectance method. In this embodiment, a laser beam is emitted from a pulse YAG laser 6 to the back surface of the specimen 5, the temperature of the surface opposite to the emitted surface is measured by the radiation thermometer 7. The temperature change of the observed surface of the specimen 5 is measured by the radiation thermometer 7, and is fitted into a thermal diffusion model. In this manner, the thermal diffusivity of the specimen 5 can be obtained. In order to measure the temperature change, a radiance temperature measurement for the specimen should be performed during a sampling interval of several tens of microseconds. Further, in order to reduce heat loss due to heat exchange between the specimen and gas, the measurement atmosphere is preferably a vacuum equal to or less than 1 mPa.

A detailed explanation of the derivation method for deriving physical properties by employing the method having above-described constitution and performing as mentioned above is described below.

Firstly, an example of the deriving method for deriving the specific heat capacity ($C_p$) and the hemispherical total emissivity ($\epsilon$) is described below.

In the method, when the current switch 3 using the field-effect transistor is switched on by the computer for controlling apparatus and data acquisition 12, a large current is supplied to the specimen 5 through the reference resistor 4 for a period shorter than one second.

At this time, the Joule heat occurring within the specimen 5 is calculated by measuring the potential difference (V) at the specimen 5, calculating the current (I) flowing through the specimen 5 based on the measurement of the potential difference at the reference resistor 4 that is connected in series to the specimen 5, and then multiplying them to determine the amount of the Joule heat.

A specimen temperature T is obtained by simultaneously measuring the radiance temperature by the radiation thermometer 7 and the normal spectral emissivity by the high-speed ellipsometer. The temperature distribution near the center of the specimen 5 that is rapidly resistive self-heated from room temperature is uniform within a short period of time, and it can be assumed that thermal radiation is the dominant factor contributing to the transfer of heat to the surrounding area of the specimen. Therefore, in the center of the specimen 5, the heat balance among the Joul heat, heat capacitance and the thermal radiation from the sample surface can be represented by the following formula (1).

$$C_p m(dT/dt) = VI - A\epsilon\sigma(T^4 - T_e^4) \quad (1)$$

In formula (1), m denotes the effective mass of the specimen, A denotes the effective surface area of the specimen, $\epsilon$ denotes the hemispherical total emissivity of the specimen, $\sigma$ denotes the Stefan-Boltzmann constant, and $T_e$ denotes the ambient temperature of the specimen.

Using a solid switch such as the field-effect transistor, the current switch 3 can carry out not only ON/OFF control but also rapid regulation of the heating current. Therefore, the temperature of the specimen can be maintained at a constant temperature for a short period by measuring the temperature of the specimen and by providing current feedback control. Under a condition wherein the temperature is constant, the left-hand side of formula (1) can be regarded as being zero, so that the hemispherical total emissivity ($\epsilon$) can be measured by using the following formula (2).

$$\epsilon = VI / \{A\sigma(T^4 - T_e^4)\} \quad (2)$$

Further, the specific heat capacity can be derived from the hemispherical total emissivity obtained by the formula (2) and the temperature change measured in the heating period by using the following formula (3), which is derived from the formula (1). In the formula (3), subscript h stands for heating time.

$$C_p = \{VI - A\epsilon\sigma(T^4 - T_e^4)\} / \{m(dT/dt)_h\} \quad (3)$$

Objects to be measured are not limited to solids. Liquid specimens can also be measured by increasing the speed of a heating period or performing the measurement in a microgravity environment. In order to reduce the measurement uncertainty in this method, it is important that the temperature of the specimen is accurately measured by the radiation thermometer 7. Therefore, in this embodiment, the normal spectral emissivity of the specimen 5 is simultaneously measured through the measurement of optical constants by the ellipsometer consisting of the detector 8 and light source 9, and compensation of the emittance is performed. Further, this method can be utilized for measuring not only the thermophysical properties but also the electrical resistivity, the normal spectral emissivity, the coefficient of thermal expansion, the melting point and the heat of fusion. Thus, various physical properties can be measured by a single apparatus.

Secondly, an example of the deriving method for deriving the thermal diffusivity ($\alpha$) is described below.

Figure 2:
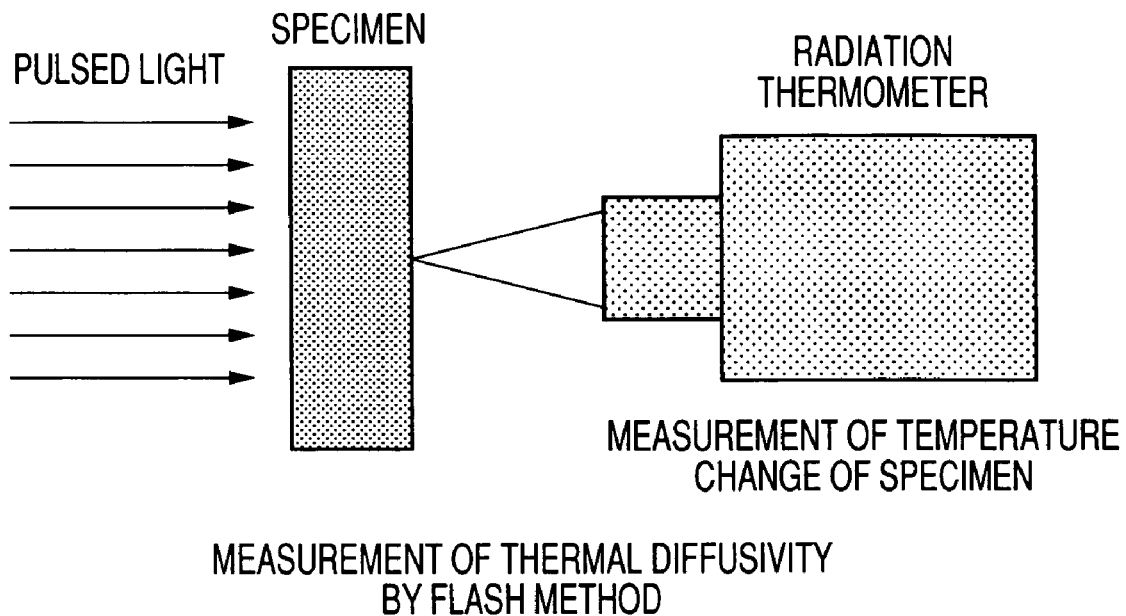
FIG. 2 is a schematic view showing an apparatus to measure a thermal diffusivity by a flash method.
Figure 3:
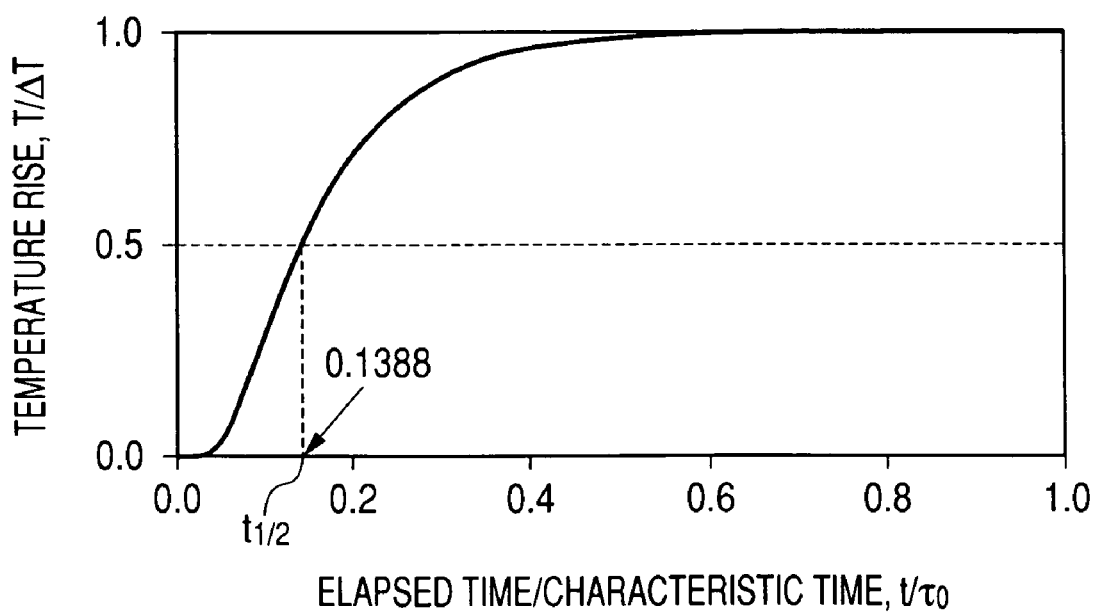
FIG. 3 is a graph showing an example of a temperature change with reference to time of the back surface of a specimen when the flash method is used.

The flash method for measuring thermal diffusivity is shown in FIG. 2. In this method, when a single pulse of light is emitted to the surface of a flat plate specimen maintained at a steady temperature, the heat induced by the emission of light to the specimen is diffused one dimensionally from the surface that is heated instantaneously and uniformly to the back side, and the heat reaches the back surface, and finally the temperature of the specimen is uniform. Since the speed of the temperature change of the back surface is defined by the formula (4) set forth below, the thermal diffusivity of the specimen can be calculated from the thickness of the specimen and the time required for thermal diffusion.

In this deriving method, the "$t_{1/2}$ method" that is a standard data analysis algorithm, can be used. In the $t_{1/2}$ method, time $t_{1/2}$ that is required until the value of the rise in the temperature of the back surface reaches $\Delta T/2$ is read from the measured curve, and the thermal diffusivity ($\alpha$) is calculated by using the following formula (4).

$$\alpha = \frac{0.1388 d^2}{t_{1/2}} \quad (4)$$

wherein, d denotes the thickness of the specimen, and $\Delta T$ denotes the difference between temperatures of the surface opposite the surface emitted with the light just before and after the completion of the thermal diffusion process.

The thermal conductivity ($\lambda$) is derived from the specific heat capacity ($C_p$), the thermal diffusivity ($\alpha$) and the density ($\rho$) of the specimen. The thermal conductivity is defined as the following formula (5).

$$\lambda = \rho \times C_p \times \alpha \quad (5)$$

The following is an example of a measuring method for obtaining parameters to be used in the above-described deriving methods.

Figure 4:
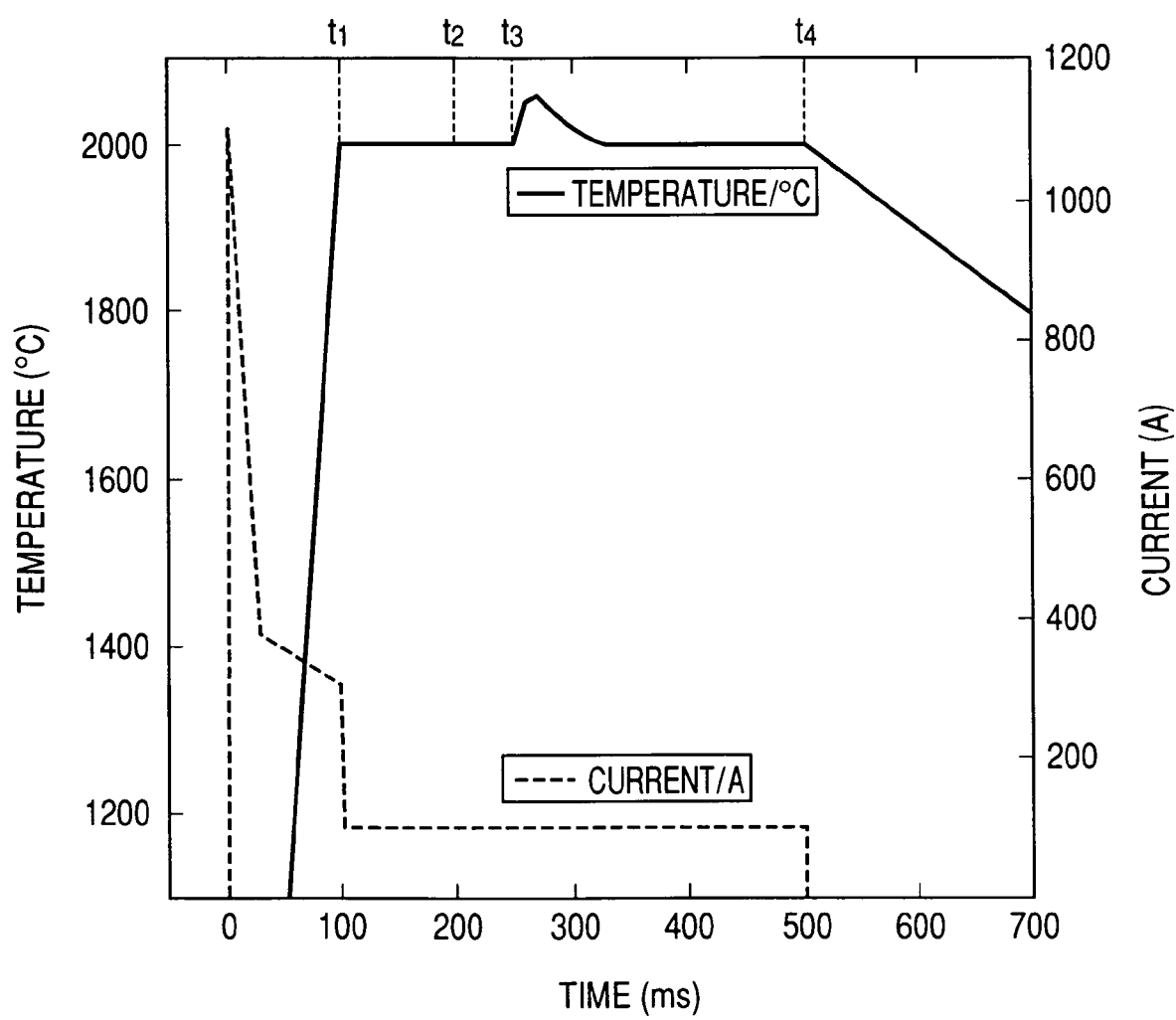
FIG. 4 is a graph showing a typical temperature change of a specimen and a change in current flowing through the specimen with reference to time, that are obtained by a high-speed measuring method for thermophysical properties of a material when a rapid resistive self-heating method is employed, and also showing an example of a temperature change of the specimen heated by a laser pulse in the determination of thermal diffusivity by a flash method.

FIG. 4 is a graph showing a typical temperature change of a specimen and a change in current flowing through the specimen with reference to time, that are obtained by a high-speed measuring method for thermophysical properties of a material when the rapid resistive self-heating method and the laser flash method is used.

The supply of a current to the specimen 5 is started at time t=0, and the feedback control of the current is performed so that the temperature of the specimen 5 is maintained at a target temperature (2000° C.) for the specimen 5. Then, the temperature is reached to the target temperature at time t=$t_1$.

Thereafter, feedback control for the current is performed to maintain the temperature of the specimen at the target temperature for the specimen 5, and the feedback control with reference to the temperature is halted at time t=$t_2$. Thereafter, the value of the current just before the feedback control was halted is maintained. At time t=$t_3$, a laser beam is emitted to the surface of the specimen 5, and the temperature change on the back surface of the specimen 5 is measured. At time t=$t_4$, the current switch 3 is turned off or all electric charges accumulated by the capacitor have been discharged, and the heating of the specimen 5 is terminated. The thermal diffusivity is calculated based on the principle of the flash method by fitting a data of the temperature change after the time t=$t_3$ into a thermal diffusion model. The specific heat capacity and the hemispherical total emissivity are also measured with the pulse electrically-heating method described above through a single process of the temperature change of the specimen 5.

EXAMPLE

The present invention is now illustrated in greater detail with reference to Example, but it should be understood that the present invention is not to be construed as being limited thereto.

Measurement was carried out to determine the thermal diffusivity of the following sample with the apparatus shown in FIG. 1.

Figure 5:
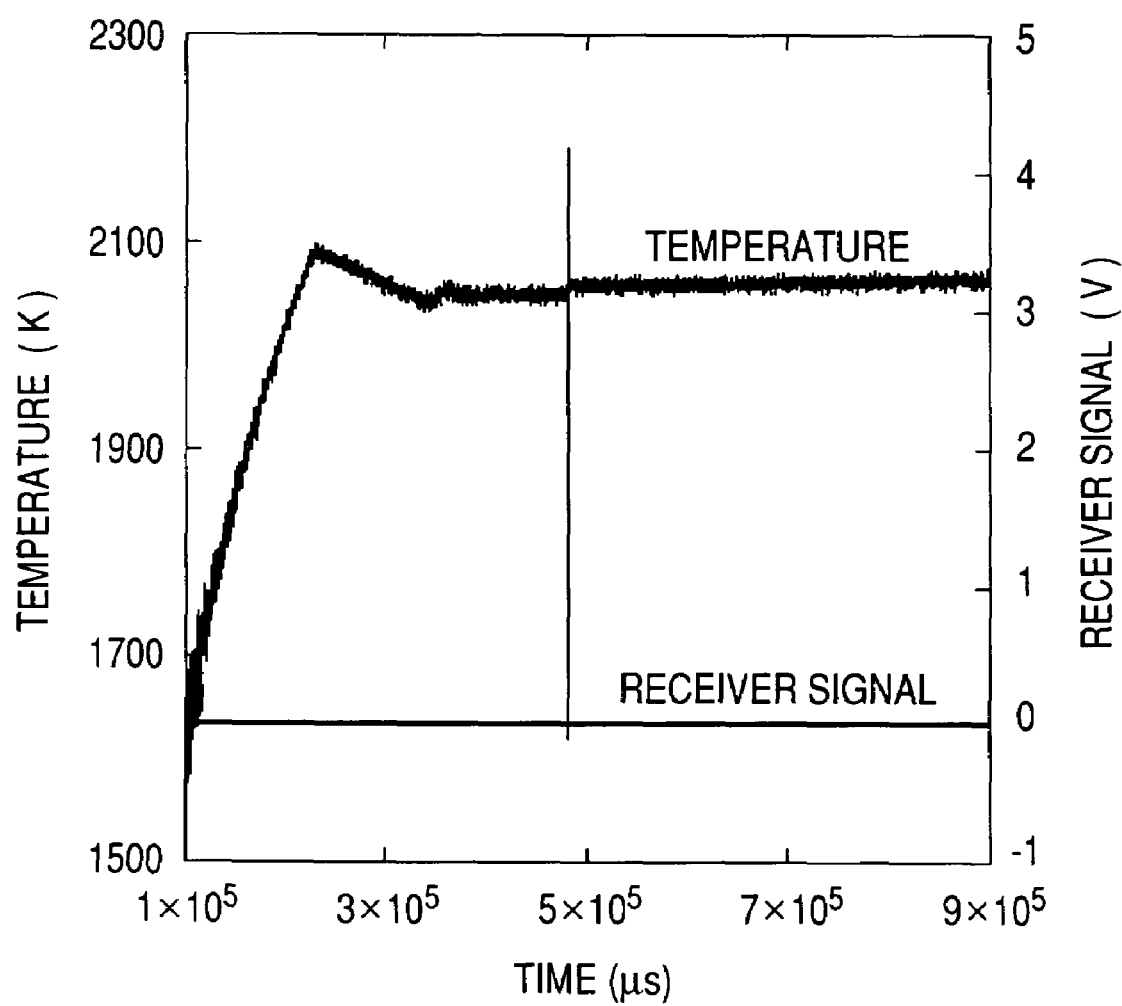
FIG. 5 is a graph showing changes of temperature of the specimen and receiver signal, which were obtained in the measurement of Example.
Figure 6:
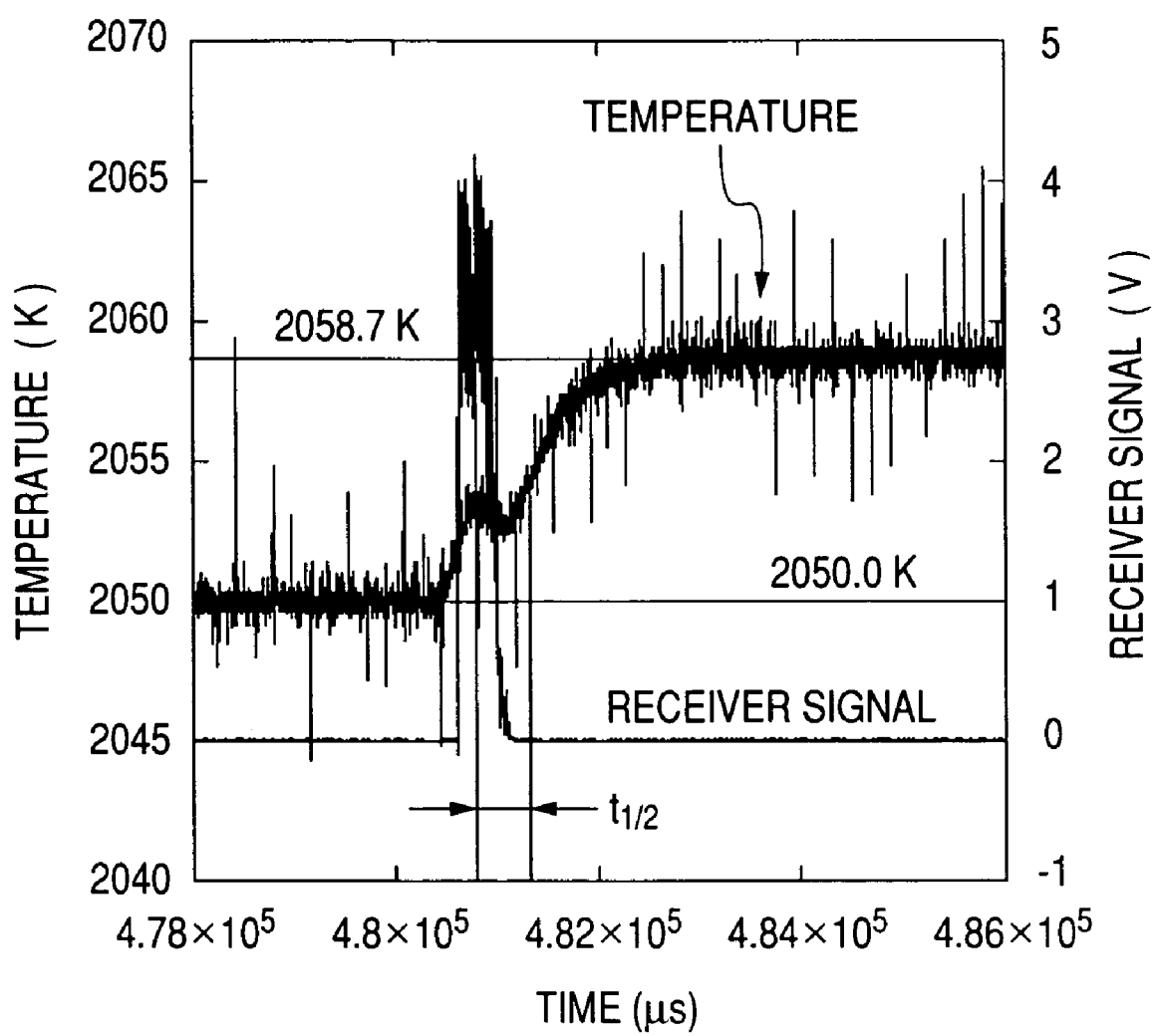
FIG. 6 is a graph showing an enlarged view of FIG. 5 at a time of emitting a laser pulse to the specimen.

Material: Molybdenum (Purity: 99.95%)
Thickness: 0.3 mm
Effective mass: 0.537 g
Effective surface area: 371 mm$^2$ Results of the measurement are shown in FIGS. 5 and 6. FIG. 6 shows an enlarged view of FIG. 5 at a time of emitting a laser pulse to the specimen. In FIGS. 5 and 6, "Receiving Signal" denotes a signal output from a photo receiver, which is detected in order to determine a time of emitting the laser pulse to the specimen. In FIGS. 5 and 6, a portion in which the signal value is drastically increased shows the time of emitting the laser pulse.

The ambient temperature in the measurement was 293 K. The constant temperature of the specimen before emitting the laser pulse to the specimen shown in FIG. 5 was 2050 K. The half time $t_{1/2}$ of thermal diffusion was measured to be 561 μm.

As a result of the above measurement, the thermal diffusivity of the specimen was determined as $2.23 \times 10^{-5}$ m$^2$s$^{-1}$ by using the formula (4).

According to a data book (Thermophysical Properties of Matter. The TPRC Data Series; Thermal Diffusivity), the thermal diffusivity of Molybdenum at 2050 K is $2.41 \times 10^{-5}$ m$^2$s$^{-1}$. Therefore, it was proved that the method of the present invention appropriately measures the thermal diffusivity of the specimen.

According to the present invention, all the thermophysical property values required for a heat transfer analysis can be efficiently measured by only one apparatus, which results in considerable reduction of measurement cost. A specimen needs to be heated in order to measure the thermophysical properties at a high temperature thereof. However, the method of the present invention can reduce the number of times of the cycle of heating and cooling process and the length of the heating period, thereby changes in the qualities of the specimen and the deterioration of the measurement apparatus caused by the exposure of the specimen and apparatus to a high temperature can be reduced. Further, according to the present invention, since a heat-insulating material and a cooling water pipe are not required, the size of the apparatus can be reduced unlike a conventional heating furnace. In addition, according to the present invention, measurements of specimens at temperatures beyond 3000° C. are enabled while the thermal diffusivity measured at the highest temperature according to the previous report is a data of graphite at approximately 2700° C.

Furthermore, the present invention can be effectively employed for the measurement of the thermophysical properties of a material such as a newly developed heat resistant alloy or carbon material, and the measurement of a heat resistant coating material.

While the present invention has been described in detail and with reference to specific embodiments thereof, it will be apparent to one skilled in the art that various changes and modifications can be made therein without departing from the spirit and scope thereof.

The present application is based on Japanese Patent Application No. 2004-056747 filed on Mar. 1, 2004, and the contents thereof are incorporated herein by reference.

What is claimed is:

1. A method for measuring thermophysical properties that comprises the following sequential steps:

rapid resistive self-heating of a specimen by using a heating current;

adjusting the heating current to maintain the specimen at a target temperature;

emitting a light to the specimen heated by the rapid resistive self-heating of the specimen while maintaining the heating current at the same value as that which maintained the specimen at a target temperature before emitting the light to the specimen;

measuring a temperature change of the specimen induced by emitting the light to the specimen;

deriving a thermal diffusivity of the specimen from the temperature change induced by emitting the light to the specimen;

measuring a temperature of the specimen when the temperature of the specimen is held at a constant temperature before emitting the light to the specimen; an electric power that is supplied to the specimen when the temperature of the specimen is held at the constant temperature; and a temperature change of the specimen induced by the rapid resistive self-heating of the specimen;

deriving a hemispherical total emissivity of the specimen from the temperature and the electric power; and deriving a specific heat capacity of the specimen from the hemispherical total emissivity and the temperature change induced by the rapid resistive self-heating of the specimen;

wherein the temperature of the specimen is controlled under a feedback control so as to have the constant temperature until just before emitting the light to the specimen.

2. The method for measuring thermophysical properties according to claim 1, wherein the heating current is maintained at a value just before the feedback control is halted during the period from the halt of the feedback control to the completion of thermal diffusion within the specimen caused by the emission of the light to the specimen.

3. The method for measuring thermophysical properties according to claim 2, wherein the light is emitted to the specimen while the heating current is maintained at the value just before the feedback control is halted.

4. An apparatus for measuring thermophysical properties that comprises:
   a rapid resistive self heating member for rapid resistive self heating of a specimen by using a heating current;
   a system for maintaining the specimen at a constant temperature;
   a system for maintaining a constant heating current flow to the specimen;
   a light emission member for emitting a light to the specimen heated by the rapid resistive self-heating of the specimen;
   a temperature measuring member for measuring a temperature change induced by emitting the light to the specimen; and
   an analysis member for deriving a thermal diffiasivity of the specimen from the temperature change induced by emitting the light to the specimen;
   wherein:
      the analysis member farther derives a hemispherical total emissivity and a specific heat capacity of the specimen;
      the hemispherical total emissivity is derived from a temperature of the specimen when the temperature of the specimen is held at a constant temperature before emitting the light to the specimen;
      an electric power that is supplied to the specimen when the temperature of the specimen is held at the constant temperature;
      the specific heat capacity of the specimen is derived from the hemispherical total emissivity;
      a temperature change of the specimen induced by the rapid resistive self-heating of the specimen; and
      the temperature of the specimen is controlled under a feedback control so as to have the constant temperature until just before emitting the light to the specimen.

5. The apparatus for measuring thermophysical properties according to claim 4,
   wherein the heating current is maintained at a value just before the feedback control is halted during the period from the halt of the feedback control to the completion of thermal diffusion within the specimen caused by the emission of the light to the specimen.

6. The apparatus for measuring thermophysical properties according to claim 5,
   wherein the light is emitted to the specimen while the heating current is maintained at the value just before the feedback control is halted.

* * * * *